United States Patent [19]

Corby

[11] Patent Number: 5,047,164

[45] Date of Patent: * Sep. 10, 1991

[54] CLEANING/DISINFECTING PROCESS AND COMPOSITION

[75] Inventor: Michael P. Corby, Ravenshead, England

[73] Assignee: Diversey Corporation, Ontario, Canada

[ * ] Notice: The portion of the term of this patent subsequent to Apr. 18, 2006 has been disclaimed.

[21] Appl. No.: 293,013

[22] Filed: Jan. 3, 1989

Related U.S. Application Data

[63] Continuation of Ser. No. 796,849, Nov. 12, 1985, Pat. No. 4,822,513.

[30] Foreign Application Priority Data

Dec. 12, 1984 [GB] United Kingdom ................. 8428564

[51] Int. Cl.$^5$ ................................................. C11D 3/43
[52] U.S. Cl. .................................... 252/106; 252/100; 252/101; 252/142; 252/146; 252/187.1; 252/187.2
[58] Field of Search ............ 252/106, 100, 101, 187.1, 252/142, 187.2, 146, 187.32, 89.1, 174.25, 173; 424/150, 149, 153, 127, 128, 162; 134/22.13, 25.3, 22.16, 25.4, 42; 422/28, 32, 37; 426/539

[56] References Cited

U.S. PATENT DOCUMENTS 4,822,513  4/1989  Cosby ................................. 252/106

*Primary Examiner*—Josephine Barr
*Attorney, Agent, or Firm*—Arnold S. Weintraub

[57] ABSTRACT

A composition characterized in that it comprises one or more interhalogens or sources thereof and one or more acids or sources thereof which are not appreciably oxidized by the interhalogen(s) is disclosed.

When diluted with water to in-use solution strength, such may be used in an ambient cleaning and/or disinfecting process in accordance with the present invention particularly for milk- or food-handling equipment.

11 Claims, No Drawings

CLEANING/DISINFECTING PROCESS AND COMPOSITION

This is a continuation of the application Ser. No. 796,849, filed Nov. 12, 1985, U.S. Pat. No. 4,822,513.

This invention relates to a cleaning/disinfecting process and composition; more particularly, it relates to the cleaning and/or disinfecting of milk- and food-handling equipment, for example general commercial dairy cleaning of pipelines, silos, filling machines and processing apparatus, and general disinfecting of food handling areas and machines, especially the "cleaning-in-place" of milking machinery.

The present system may be used for the cleaning and/or disinfecting of apparatus in farm and commercial dairies of both the process and liquid milk type. Such apparatus includes, for example, milking machines, collection tankers used to transport milk in bulk, bulk milk holding silos, milk meters, general pipework, bottle and carton filling machines, butter making machinery, yoghurt manufacturing plant and cheese making machinery. Generally, such apparatus needs to be cleaned hot (60°-85° C.). The present invention provides a means by which such apparatus may be cleaned and disinfected or merely disinfected after cleaning, but at ambient temperatures. The present compositions may be used as cleaning and disinfecting solutions or as acidic disinfectants alone.

For purposes of illustration only, the present invention will be generally described in relation to milk-handling equipment.

Currently, it is common practice to clean, for example, pipes and containers which have to come into contact with milk using solutions of caustic soda and/or potash with sodium hypochlorite, sequestrants and wetting agents. Generally, such solutions must be used hot (60°-85° C.) and are somewhat hazardous at high pH (11-14).

In this field, it is important that the results are both visually and microbiologically acceptable. There is also a public safety aspect and in the U.K. the Milk and Dairy Regulations 1959 must be satisfied. Before a new system may be adopted, it must be approved under the auspices of MAFF (Ministry of Agriculture, Fisheries and Food). A particularly demanding test for novel systems, is the so-called Lisboa tube test wherein for cold cleaning an in-use formulation and a ⅔ strength solution must each at 5° C. reduce the bacteria on the inside of the milk-soiled tubes as well as or better than standard sodium hypochlorite/sodium carbonate solutions at 44° C. (Reference may be made to FIL IDF 44:1967 for further information.) Until now, no commercially available cold cleaning system has passed this 5° C. test.

A new system has now been found which not only satisfies the official Lisboa tube test, but also results in an acceptably visually clean environment. Additionally, the new system being acidic, hard water scale and milkstone problems are obviated. Most importantly, the present system may be used at ambient temperature. In a milking parlour, for example, the routine would usually be that, after several cold cleans in accordance with the present invention, a hot caustic clean would be effected. For example, the regular cleaning might be carried out using the present system on, say, six occasions and then on the seventh a conventional hot clean would be used. The present system has the advantage that, on this basis, up to about 86% of current energy expenditure for heating cleaning solutions for a milking parlour may be saved, while obtaining equivalent microbiological results. Depending on requirements, periodic hot cleaning may be necessary less often. It is possible that by taking advantage of the benefits of the present invention a user might only need to use a hot clean once a week or even once a month, again depending on requirements. This should result in overall financial gains for the user, apart from the convenience. In some instances, the advantages of the present invention may be enhanced by a preliminary cleaning step. Particularly advantageous results may be obtained by utilising a so-called pre-rinse, more specifically a detergent pre-rinse. In some cases, synergism may be noted between the pre-rinse and the detergent cycle. Suitable soluble surfactants for such purpose are known. (Given the context, it is appropriate to refer to the surfactants as detergents.)

The present invention relates to a composition which comprises one or more interhalogens or sources thereof and one or more acids or sources thereof which are not appreciably oxidised by the interhalogen(s).

The interhalogen may be iodine chloride, iodine trichloride, iodine bromide, bromine chloride or a mixture thereof. Generally, iodine chloride is preferred. Such compositions may comprise interhalogen up to the limit of solubility, but generally comprise up to 25%, preferably up to 10%, more particularly from 2 to 3%, by weight, of interhalogen.

For convenience of formulation, the present compositions generally comprise an interhalogen-solubilising component. This may be organic in nature, but is preferably selected from appropriate, generally metallic, halides and hydrohalic acids or equivalents thereof. In the case of iodine chloride, iodine trichloride, iodine bromide or bromine chloride, a metal chloride or hydrochloric acid may be used, while in the case of iodine bromide it is also possible to use a metal bromide or hydrobromic acid. Up to 25%, by weight, of solubilising component may be present.

The acids which are suitable for use for the purposes of the present invention include nitric acid, phosphoric acid, hydrochloric acid, sulphamic acid, sulphuric acid or mixtures thereof. It is preferred to use nitric acid. The present compositions may comprise up to 95%, preferably up to 40%, more particularly from 24 to 26%, by weight of acid. The acid component must not be appreciably oxidised by the interhalogen and may be regarded as relatively strong.

A preferred combination for the basis of the present invention comprises iodine chloride and nitric acid.

Generally, the present compositions comprise one or more conventional excipients, which must, of course, be compatible with other components and the intended use. Suitable excipients may include dispersing agents, for example polyacrylates, such as "Dispex N 40" (Allied Colloids), surfactants, which are generally of a low-foam type in view of the intended application, such as "Dowfax 3B2" (Dow), corrosion inhibitors and tracers. Each auxiliary may be present in an amount of up to 5%, by weight.

The present compositions are commonly provided in the form of an aqueous liquid concentrate, but may also be in solid form for dissolution in water. Particularly in the latter case, it may be convenient to utilise a solid source of acid, such as a bisulphate.

For use, the present compositions are generally diluted with water so that an in-use solution may comprise up to 5%, by weight, of the above composition.

The present invention also relates to the production of such compositions and solutions.

As mentioned above, the present compositions, more particularly dilute solutions thereof, are particularly effective for the cold-cleaning and/or disinfecting of, for example, milk- or food-handling equipment, such as milking machinery.

The present invention further relates to a cleaning and/or disinfecting process which comprises the use of such a solution.

It may be beneficial to use a detergent simultaneously.

Optionally, preliminary cleaning, such as a detergent pre-rinse, may be effected. Bearing in mind the application envisaged, one or more low-foam or defoamed detergents is/are preferably used. Conventional non-ionic, cationic, anionic or amphoteric detergents may be used, non-ionic surfactants being preferred. Generally, up to 5% $v/v$, preferably about 0.05% $v/v$, of detergent is used.

More particularly, solutions of low foaming surfactants, in particular non-ionic surfactants having an HLB similar to that of milk fat, i.e. 8 when used as a pre-rinse to a detergent cycle with the present, interhalogen/acid combinations have been found to improve the overall detergency considerably. The use rates of these surfactants may vary from 10 to 5000 ppm, typically about 250 ppm. Such markedly improves the visual appearance of the milking parlour after the cleaning cycle. An example of a surfactant of interest is a $C_{12-14}$ alcohol with 4-5 moles of ethylene oxide. Prerinsing, more particularly non-ionic pre-rinsing, may also be advantageous in general cleaning situations.

For example, a conventiona milking parlour may be cleaned and/or disinfected by circulating a 0.5% $v/v$ solution for from 10 to 15 minutes at ambient temperature.

Certain preferred embodiments of the present invention will now be described in more detail.

| Example I | |
|---|---|
| Iodine chloride | 2.2%, by weight |
| Hydrochloric acid (28% $w/w$) | 2.5%, by weight |
| Nitric acid (60% $w/w$) | 40.0%, by weight |
| Water | 55.3%, by weight |

The nitric and hydrochloric acids were added, with stirring, to the water, followed by the iodine chloride. A homogeneous yellow liquid was obtained containing dichloroiodate ions: $ICl + Cl^- \rightarrow ICl_2^-$.

Iodine chloride may be obtained in a variety of ways usually involving the oxidation of iodide or iodine by iodate in the presence of chloride ions under highly acidic conditions; e.g. 4-6N HCl. Such is akin to the Andrews titration (JACS, 1903, 25, 756):

$$2I^- + IO_3^- + 3Cl^- + 6H^+ \rightarrow 3ICl + 3H_2O$$

Iodine chloride is commercially available, but is easily decomposed and difficult to handle. An alternative safer, more convenient and probably cheaper way of preparing such a formulation is to produce the iodine chloride which is converted to dichloroiodate anion, in situ from the reaction of an iodide, iodate and chloride in the presence of acid:

$$2I^- + IO_3^- + 6Cl^- + 6H^+ \rightarrow 3ICl_2^- + 3H_2O \qquad (I)$$

Another possibility involves the acidification of iodine/iodide in sodium hypochlorite solution. (In this case, particular care is necessary regarding proportions as chlorine may be evolved.)

| Example II | |
|---|---|
| Iodine | 1.3%, by weight |
| Sodium hydroxide | 1.0%, by weight |
| Potassium iodate | 0.57%, by weight |
| Hydrochloric acid (28% $w/w$) | 4.3%, by weight |
| Nitric acid (60% $w/w$) | 40.0%, by weight |
| Water | 52.83%, by weight |

The sodium hydroxide, which is used merely to facilitate dissolution of the iodine, was added to the water, with stirring, followed by the iodine until complete solution was obtained in:

$$3I + 6OH^- \rightarrow IO_3^- + 5I^- + 3H_2O \qquad (II)$$

Then extra potassium iodate required for complete reaction was added and mixed until dissolved. The hydrochloric and nitric acids were then added, with stirring, and stirring was continued until a homogenous yellow liquid was obtained in accordance with the above reaction scheme (1).

| Example III | |
|---|---|
| Iodine | 1.3%, by weight |
| Sodium hydroxide | 1.0%, by weight |
| Potassium iodate | 0.57%, by weight |
| Hydrochloric acid (28% $w/w$) | 4.3%, by weight |
| Nitric acid (60% $w/w$) | 40.0%, by weight |
| Water | 51.83%, by weight |
| Dispersing agent "Dispex N 40" (sodium salt of low molecular weight (~3500) polyacrylic acid) | 1.0%, by weight. |

This example generally corresponds to Formulation 2, except that a dispersing agent was added with a corresponding decrease in the amount of water. (Commercial products would normally comprise such conventional additives.)

Although iodine chloride is the preferred interhalogen for the present purposes, the present invention is not so-limited. Similarly, nitric acid is merely the preferred acid.

| Example IV | |
|---|---|
| Iodine bromide | 2.00%, by weight |
| Sodium bromide | 5.00%, by weight |
| Phosphoric acid (75% $w/w$) | 50.00%, by weight |
| Water | 43.00%, by weight |

The sodium bromide was dissolved, with stirring, in the water and the phosphoric acid blended in. Then, the iodine bromide was mixed in to obtain a clear orange solution.

Although the present compositions are commonly provided as aqueous liquid concentrates, they may, as mentioned above, be in solid form for dissolution in water.

| Example V | |
|---|---|
| Potassium hydrogen sulphate | 50.0%, by weight |
| Potassium chloride | 49.0%, by weight |
| Iodine monochloride | 1.0%, by weight |

For such solid formulations, the ingredients may be compounded and mixed in a conventional manner.

Generally, a single interhalogen component is used, but combinations are possible.

| Example VI | |
|---|---|
| Iodine chloride | 1.0%, by weight |
| Iodine bromide | 1.0%, by weight |
| Hydrochloric acid (36% w/w) | 30%, by weight |
| Hydrobromic acid (50% w/w) | 20%, by weight |
| Water | 48%, by weight |

Such mixed interhalogen products may be prepared as illustrated above.

Iodine chloride is the preferred interhalogen, but others share the utility.

| Example VII | |
|---|---|
| Iodine trichloride | 1.0%, by weight |
| Hydrochloric acid (36%, w/w) | 99%, by weight |

Such may be obtained by analogous methods.

Reference was made above to the Lisboa Tube Test. The results for Formulation 3 as presented by the Laboratory of the Government Chemist are as follows:

| Example VIII | | |
|---|---|---|
| | log (colony count/ml) | |
| Disinfectants | Normal Strength | $\frac{3}{8}$ Normal Strength |
| Hypochlorite - 0.25% v/v (4 fl. oz./10 gallons) | 1.966 (300 ppm available chlorine) | 3.181 (200 ppm available chlorine) |
| Formulation 3 - 0.5% v/v (8 fl. oz./10 gallons) | 2.509 | 3.447 |

Application of analysis of variance plus the Duncan's Multiple Range Test to the data demonstrates that there are not significantly (at the 5% level) more bacteria surviving after the use of Formulation 3 at 0.5% v/v (8 fl. oz./10 gallons) than with hypochlorite at 300 ppm available chlorine and similarly treatments using $\frac{3}{8} \times 0.5\%$ v/v (8 fl. oz/10 gallons) of Formulation 3 is not significantly different at the 5% level to hypochlorite at 200 ppm available chlorine.

At in-use strength, the present compositions give acceptable cleaning and/or disinfecting. Such formulations are stable for at least several years even at elevated temperature. The in-use solutions are acceptably compatible with materials commonly encountered.

EXAMPLE IX

For purposes of illustration, a one jar experimental milking parlour was twice soiled with 5 liters of raw milk. After 5 minutes, to allow the milk residues to dry on to the surfaces, the parlour was rinsed and cleaned in a conventional manner. The parlour received a bacteriological rinse according to BS 4285.

Some typical data is given below. Cleaning was effected daily using "Deosan New Delex" and the results are shown in the first column of the following Table. ("Deosan New Delex" is an approved Diversey hot circulation cleaner, which consists essentially of caustic soda, hypochlorite and a scale control agent.) The second column indicates the results obtained using Formulation 3 in accordance with the present invention. After those asterisked, a conventional hot clean using "Deosan D60" was also carried out. ("Deosan D60" is an approved Diversey product, which is provided as a powder containing essentially caustic soda, a chlorine-release agent, sodium tripolyphosphate and a surfactant.) The third column relates to the use of the present system at a higher rate, but only on alternate days.

| log (counts m$^{-2}$) | | |
|---|---|---|
| "Deosan New Delex" approx. 0.31% v/v (5 fl. oz/10 gallons) (77-82° C.) | Formulation 3 approx. 0.31% v/v) (5 fl. oz/10 gallons)(Ambient) | Formulation 3 0.5% v/v (8 fl. oz./10 gallons) (Ambient) |
| 5.437 | 5.543 | 4.326 |
| 4.505 | 5.851 | — |
| 5.201 | 6.322 | 5.960 |
| 5.201 | 6.406 | — |
| 5.593 | 6.198 | 5.864 |
| 5.648 | 6.250* | — |
| 6.309 | 4.806 | 6.210 |
| 6.207 | 6.640 | — |
| 6.025 | 6.348 | |
| 5.473 | 6.505 | |
| | 6.574 | - indicates no bacteriological rinse carried out |
| | 6.161* | |
| | 4.627 | |
| | 4.627 | |
| | 5.387 | |
| | 6.181 | |
| N = 10 | n = 16 | n = 4 |
| x̄ = 5.564 | x̄ = 5.902 | x̄ = 5.590 |
| $\sigma_{n-1}$ = 0.536 | $\sigma_{n-1}$ = 0.692 | $\sigma_{n-1}$ = 0.855 |

Applying a students t-test to the above data shows that there is no significant difference between the bacteriological rinse results on Formulation 3 used at 0.5% v/v (8 fl. oz/10 gallons) and ambient temperatures and those on "New Delex" of approx. 0.31% v/v (5 fl. oz/10 gallons) at 77°-82° C.

EXAMPLE X

During the test, the general appearance of the parlour was satisfactory.

As part of the approvals protocol for cold cleaners a series of MAFF monitored trials have been carried out. Milking machines were monitored both visually and microbiologically using the Full Plant Rinse Technique described in British Standard 4285: 1968, 2.2.2.7, pages 32-37. all times during the trial protocol, the plant remained visually acceptably clean. Results of the full plant rinses on both hot and cold cleaning are shown in the following Table.

Results of plant rinse counts/m² (log values).

Hot cleaning using Deosan D60 80°-85° C. 0.375% w/v (6 oz/10 gallons)

| Farm | 1 | 2 | 3 | 4 |
|---|---|---|---|---|
| | 6.43 | 6.49 | 6.08 | 7.20 |
| | 5.88 | 6.58 | 6.45 | 6.77 |
| | 6.67 | 6.92 | 6.96 | 6.90 |
| | 5.76 | 6.49 | 6.89 | 6.89 |
| | 6.49 | 5.95 | 6.88 | 6.94 |
| | 6.34 | 6.04 | 7.11 | 7.09 |

-continued

| Farm | 1 | 2 | 3 | 4 |
|------|------|------|------|------|
|      | 6.93 | 5.95 | 6.80 | 7.42 |
|      | 7.12 | 6.83 | 7.09 | 6.91 |

Cold cleaning routine-results after 6th cold clean

| 5.97 | 5.55 | 5.61 | 6.20 |
|------|------|------|------|
| 6.49 | 5.88 | 5.76 | 6.45 |
| 6.24 | 5.18 | 5.56 | 6.53 |
| 6.49 | 5.84 | 4.95 | 6.49 |
| 6.63 | 5.11 | NR   | 6.11 |
| 6.16 | 5.88 | 5.78 | 6.11 |
| 5.80 | 5.18 | 7.56 | 6.92 |
| 5.80 | 6.55 | 5.41 | 6.67 |
| 6.50 | 6.57 | 5.17 | 6.23 |

| Means of Rinses from Above Table | | | | |
|---------|-------|-------|-------|-------|
| Farm    | 1     | 2     | 3     | 4     |
| Hot D60 | 6.578 | 6.406 | 7.015 | 6.783 |
| Cold Routine | 6.231 | 5.749 | 6.412 | 5.725 |

EXAMPLE XI

An assessment of the microbiological effectiveness of the present cold cleaning system has been carried out at the West of Scotland College of Agriculture, Auchincruive, Ayr, Scotland. A summary of the results is shown below.

| Plant Rinse Counts/m$^2$ (log values) | |
|---|---|
| Mean of 23 results using Hot D60 at 0.375% w/v (6 oz/10 gallons) | 6.648 |
| Mean of 13 results after 6th cold clean using Formulation 3 at 0.5% v/v (8 fl. oz/10 gallons) | 6.101 |

I claim:

1. A process for preparing an acid-based cleaning/disinfecting composition containing a stable interhalogen, $ICl_2-$, said process comprising the in situ preparation of $ICl_2-$ by:
   i) reacting in solution a source of $I-$ with a source of $Cl-$ in the presence of up to 95 percent by weight of solution of an acid selected from the group consisting of nitric acid, phosphoric acid, hydrochloric acid, sulfonic acid, sulfuric acid and mixtures thereof, to produce up to 25 percent by weight of solution of stabilized $ICl_2-$ in an acid medium which is not appreciably oxidized by the interhalogen.

2. The process of claim 1 further comprising:
   ii) adding up to 25 percent by weight of solution of a solubilized component for $ICl_2-$ selected from the group consisting of metallic halides and hydrochloric acids.

3. The process of claim 2 further comprising:
   iii) adding up to 5 percent by weight of solution of a dispersing agent.

4. The process of claim 2 wherein said solubilizing component is a metal chloride.

5. The process of claim 2 wherein said solubilizing component is hydrochloric acid.

6. The process of claim 1 wherein said acid is nitric acid.

7. The process of claim 6 wherein said acid is present in an amount up to 40 percent by weight.

8. The process of claim 6 wherein said acid is present in an amount between about 24 to about 26 percent by weight.

9. The process of claim 1 wherein said interhalogen is present in an amount up to about 10 percent by weight.

10. The process of claim 1 wherein said interhalogen is present in an amount between about 2 to about 3 percent by weight.

11. The process of claim 3 further comprising:
    iv) adding up to 5 percent by weight of solution of an excipient selected from the group consisting of: a surfactant, a corrosion inhibitor and a tracer.

* * * * *